United States Patent [19]

Caruso

[11] 4,261,844

[45] Apr. 14, 1981

[54] GREASE COMPOSITIONS

[75] Inventor: Gerard P. Caruso, New Orleans, La.

[73] Assignee: Shell Oil Company, Houston, Tex.

[21] Appl. No.: 106,057

[22] Filed: Dec. 21, 1979
(Under 37 CFR 1.47)

[51] Int. Cl.$^3$ .......................... C01M 5/20; C01M 5/12; C01M 7/32; C01M 7/30
[52] U.S. Cl. ................................................ 252/51.5 A
[58] Field of Search ................................... 252/51.5 A

[56] References Cited

U.S. PATENT DOCUMENTS

| | | | |
|---|---|---|---|
| 2,710,839 | 6/1955 | Swakon et al. | 252/51.5 A |
| 3,242,210 | 3/1966 | Dreher et al. | 252/51.5 A |
| 3,243,372 | 3/1966 | Dreher et al. | 252/51.5 A |
| 3,401,027 | 9/1968 | Dreher et al. | 252/51.5 A |
| 3,846,314 | 11/1974 | Dreher et al. | 252/51.5 A |

*Primary Examiner*—Herbert Levine
*Assistant Examiner*—Irving Vaughn
*Attorney, Agent, or Firm*—Albert J. Adamcik

[57] ABSTRACT

Polyurea grease compositions containing the reaction product of certain diisocyanates and specified amines, particularly N,N-bis(3-amino propyl)methylamine, and having improved mechanical properties, are disclosed.

12 Claims, No Drawings

GREASE COMPOSITIONS

BACKGROUND OF THE INVENTION

The requirement that grease compositions provide adequate lubrication at high temperature for extended periods of time has become increasingly important. For this reason, many grease compositions contain a variety of organic thickening agents, such as those containing multiple uriedo or urea functional groups. A number of patents, e.g., U.S. Pat. Nos. 3,846,314; 3,242,210; 3,243,372 and 3,401,027 disclose specialized thickening agents for various fluids, the thickening agents being obtained from a three component reactant mixture comprising a monoamine, a polyamine and a diisocyanate, or a monoisocyanate, a diisocyanate and a polyamine.

As a general rule, the reaction product comprises a mixture of urea-containing species of varying chain length and urea content. However, by careful control of reaction variables such as, e.g., the relative quantities of reactants employed, the reaction temperature and the rate and order of reactant mixing, a product may normally be obtained which predominates in one polyurea species. The polyurea reaction is preferably carried out in situ in the grease oil base, and the product may be utilized directly as a grease.

While greases thickened with polyurea thickeners are in many respects superior to older lubricants in severe service application, especially with regard to maintainance of grease consistency at high temperatures, such greases suffer several disadvantages which limit their usefulness under practical service conditions. For example, in some instances, the product must be subjected to rotor/stator shear or high pressure Manton Gaulin milling to get the best penetration yield for the amount of gellant used. Again, while polyurea thickened greases show excellent retention of mechanical properties at high temperature (70° C. or above) and high or low shear, they tend to soften considerably when subjected to low shear at ambient temperature ranges (20°-30° C.). In fact, the tendency to soften at ambient temperature under low shear can be so great that the grease can, when subject to mechanical working under these conditions, undergo a change in penetration grade, e.g., from a No. 2 NLGI penetration grade to a No. 1 NLGI penetration grade. This change in penetration grade at ambient temperature under low shear is particularly troublesome since it may occur under practical use conditions when the grease is transferred from the original shipping container or is otherwise stirred or handled. Consequently, normal handling of the grease in making it available to the ultimate consumer may change its consistency to such extent that it is no longer the desired penetration grade for the intended application. While it is true that the change in consistency is reversible, in that the softened grease can be subjected to high shear at high temperatures (conditions used in the original grease preparation) to return the grease to its original consistency, this reversal often requires that the softened grease be shipped back to the formulator for reprocessing. Finally, not all polyurea thickened greases demonstrate good fretting corrosion properties.

Accordingly, a need has existed for the development of a polyurea thickened grease formulation which possesses improved mechanical properties. The invention satisfies that need, and provides improved polyurea thickened grease compositions having enhanced hardness, and improved shear and fretting corrosion properties.

SUMMARY OF THE INVENTION

More particularly, the invention relates to novel polyurea compositions, and to novel grease compositions containing such polyureas. The novel polyurea compositions of the invention contain compounds having the formula

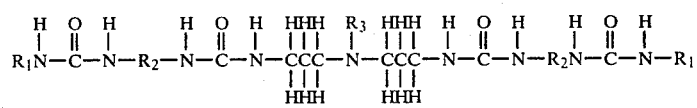

wherein $R_1$ is the same or different hydrocarbyl containing 3 to 30 carbon atoms, preferably 10 to 30 carbon atoms;

$R_2$ is the same or different hydrocarbylene having from 2 to 30 carbon atoms, preferably 6 through 15 carbon atoms;

and $R_3$ is selected from methyl, ethyl, or n-propyl, preferably methyl.

As referred to herein, hydrocarbyl is a monovalent organic radical composed of hydrogen and carbon and may be aliphatic, aromatic or alicyclic or combinations thereof, e.g., aralkyl, alkyl, aryl, cycloalkyl, alkylcycloalkyl, etc., an may be saturated or olefinically unsaturated (one or more double bonded carbons, conjugated or nonconjugated). The hydrocarbylene, as limited in $R_2$ above, is a divalent hydrocarbon radical which may be aliphatic, alicyclic, aromatic or combinations thereof, e.g., alkylarylene, aralkylene, alkylcycloalkylene, cycloalkylarylene, etc., having its two free valences on different carbon atoms.

The polyurea compounds of the invention may be prepared by reacting a diisocyanate having the formula $OCN-R_2-NCO$, wherein $R_2$ is as described, supra, a polyamine having the formula $NH_2-C_3H_6N-R_3-C_3H_6NH_2$ wherein $R_3$ is selected from methyl, ethyl, or n-propyl and a monoamine ($NH_2R_1$) wherein $R_1$ is as described, supra. Although mixed monoamines, or more than one monoamine may be employed as the monoamine reactant, it is preferred that the monoamine reactant be of substantially one component.

The reaction is preferably conducted by rapidly contacting the three reactants in a reaction vessel at a suitable temperature, e.g., between about 60° to 320° F., preferably from 80° to 300° F. Generally, the reaction will proceed virtually instantaneously, although contact times of up to five hours or more may be utilized. Contact times of from 0.001 seconds to 3 hours may be used, with contact times of from 0.01 seconds to 3 hours being preferred. Alternately, the polyamine and the monoamine may be mixed together, and the diisocyanate added to the mixture.

As indicated, the reaction product comprises a mixture of urea-containing species of varying chain length and urea content. However, by careful control of reaction variables such as, e.g., the relative quantities of reactants employed, the reaction temperature and the rate and order of reactant mixing, a product may normally be obtained which predominates in one desired species. In order to achieve the most desirable reaction product, the respective molar proportions or ratio of polyamine, diisocyanate, and monoamine should approximate 1, 2, and 2, although varying proportions to a minor extent should achieve an acceptable product. Those skilled in the art will recognize, of course, that commercially available reaction materials are rarely substantially pure, the reactants often containing varying proportions of isomers, related compounds, etc,. For example, one commercially available toluene diisocyanate, used in the examples herein, is a mixture of isomers, and contains up to 20 percent by weight of 2,6-toluene diisocyanate, the remainder being substantially 2,4-toluene diisocyanate. Nonetheless, all weights and calculations based thereon, herein given, are stated as if pure materials were employed. The reaction is preferably carried out in situ in the grease oil base or base vehicle, and the reaction product may be utilized directly as a grease. Accordingly, the invention, in its preferred form, comprises a major portion of a lubricating oil base vehicle and a minor amount of the product obtained by reacting the species mentioned, the reactants being added simultaneously or sequentially to the reaction vessel, in the manner indicated.

The amount of the compounds employed for grease thickening is, as mentioned, a minor amount, the precise amount employed being dependent on the base vehicle, the properties desired, etc. In general, the determination of the precise amounts to be employed are well within the ability of those skilled in the art, the amount employed being sufficient to thicken the vehicle to the consistency of a grease. Normally, amounts of from 2 percent to 18 percent by weight will be employed, with amounts of from 9 to 12 percent by weight being preferred.

DETAILED DESCRIPTION OF THE INVENTION

The following examples are illustrative of the invention.

EXAMPLE I

In this example, 23.1 grams of N,N-bis(3-amino propyl)methyl amine were added to a solution of 86.55 grams of stearylamine in 667.5 grams of 500 SUS at 100° F. HVI Neutral Oil at ambient temperature of 80° F. The mixture was then added, while mixing, to a second vessel containing 55.35 grams of toluene diisocyanate in 667.5 grams of 500 SUS at 100° F. HVI Neutral Oil. After stirring approximately 30 seconds, the reacted material was allowed to cool to 77° F. The grease was then worked at 60, 120, and 180 strokes, a portion was rotor/stator milled, and another portion was Gaulinized at 5000 PSIG. Table I shows the results of the ASTM penetrations taken on the grease under the heading N,N, bis AP.

EXAMPLE II

For comparison, the above procedure was repeated employing 11.63 grams of ethylene diamine, 97.05 grams of stearylamine in 667.5 grams of 500 SUS at 100° F. HVI Neutral Oil, and 56.29 grams of toluene diisocyanate in 667.5 grams of 500 SUS at 100° F. HVI Neutral Oil. The results of the ASTM penetrations are shown in Table I under the heading EDA.

TABLE I

| Conditions: Ambient temperature, minimum shear in mixing, 11 percent by weight thickener. | | |
|---|---|---|
| | N,N,bis-AP | EDA |
| Shear Rate | Simple hand mixing | Simple hand mixing |
| Unworked | 310 | 274 |
| 60 | 271 | 290 |
| 120 | 280 | 294 |
| 180 | 281 (Grainy) | 308 (Grainy) |
| | Rotor/stator milling | Rotor/stator milling |
| Unworked | 235 | 250 |
| 60 | 247 Smooth | 272 Smooth |
| 120 | 252 | 286 |
| Shear rate | 509 Sec$^{-1}$ | 509 Sec$^{-1}$ |
| Pressure | 75 PSIG | 75 PSIG |
| | Manton Gaulin Milling | Manton Gaulin Milling |
| Unworked | 242 | 253 |
| 60 | 246 | 274 |
| Shear Rate | 41,199 Sec$^{-1}$ | 41,199 Sec$^{-1}$ |
| Pressure | 5000 PSIG | 5000 PSIG |

The results of experiments 1 and 2 show that the compound of the invention provides a harder product than similar prior art materials.

EXAMPLE III

In this example, 23.1 grams of N,N-bis(3-amino propyl) methylamine were added to an oil solution of 36.55 grams of stearylamine in 500 SUS at 100° F. HVI Neutral Oil at ambient temperature. The mixture then was added to a vessel containing 55.35 grams of toluene diisocyanate (TDI) in 667.5 grams of the same oil at ambient temperature. At the time of addition of the amine solution to the TDI solution, the circulating pump was started and the reactants were recycled at a rate of 36 pounds per minute for 30 seconds, after which the contents of the vessel were pumped into a container at a temperature of 122° F. Since ambient was 92° F., the rise in temperature from the exothermic reaction was about 30° F. The worked penetration of this grease was found to be 288. Results of the experiment are shown in Table II.

EXAMPLE IV

The procedure of Example III was repeated except that the starting materials were elevated to a temperature of 170° F. The 60 stroke worked penetration was 289. Results are shown in Table II.

EXAMPLE V AND VI

The procedures of Examples III and IV, respectively, were repeated, utilizing the same total percent of thickener, except that 11.635 grams of ethylene diamine were employed instead of N,N,-bis(3-aminopropyl)methylamine, 97.053 grams of stearylamine, and 56.293 grams of toluene diisocyanate were used. The 60 stroke worked penetration for the sample made at 92° F. was 364 while the worked penetration for the sample made at 170° F. was 357. Results are shown in Table II.

TABLE II

| COMPOUND | N,N,bis-AP | N,N,bis-AP | EDA | EDA |
|---|---|---|---|---|
| thickener (percent by weight) | 11% | 11% | 11% | 11% |
| polyamine | 23.1 | 23.1 | 11.6325 | 11.6325 |
| stearylamine | 86.55 | 86.55 | 97.053 | 667.5 |

TABLE II-continued

| COMPOUND | N,N,bis-AP | N,N,bis-AP | EDA | EDA |
|---|---|---|---|---|
| 500 SUS @ 100° F. HVI Neut. | 667.5 | 667.5 | 667.5 | 667.5 |
| Toluene Diisocyanate | 55.35 | 55.35 | 56.293 | 56.293 |
| 500 SUS @ 100° F. HVI Neut. | 667.5 | 667.5 | 667.6 | 667.6 |
| Processing time (Viking system) | 30 sec | 30 sec | 30 sec | 30 sec |
| Processing Shear Rate | 164 sec$^{-1}$ | 164 sec$^{-1}$ | 164 sec$^{-1}$ | 164 sec$^{-1}$ |
| Final Processing Temp °F. | 122° F. | 168° F. | 120° F. | 162° F. |
| Unworked ASTM | 259 | 265 | 341 | 319 |
| @ 60 | 288 | 289 | 364 | 357 |
| @ 20 | 287 | 289 | 365 | 364 |
| @ 180 | 286 | 288 | 372 | 366 |
| Appearance | smooth | smooth | smooth | smooth |
| 5000 PSIG Manton Gaulin @ ambient UNW/60 ASTM First Pass | 250/253 | 243/251 | 307/327 | 317/335 |
| Δ PEN 180 str-60 str Gaulin | 33 | 36 | 35 | 31 |
| 5000 PSIG Manton Gaulin @ ambient UNW/60 ASTM Second Pass | — | — | 281/303 | 315/328 |
| 5000 PSIG Manton Gaulin @ ambient UNW/60 ASTM Third Pass | — | — | 282/295 | — |

The results indicate that even with extra shear the pen yield for EDA compositions is less when compared with the compositions of the invention. The novel compositions of the invention have increased efficiency so that less thickener is required to thicken the lubricating oil base vehicle to a given penetration grade. The increase in grease yield based on the quentity of thickener employed has the secondary advantage of improving the low temperature properties of the grease because of the reduction in gellant content and concomitant increase in oil content. Again, the compositions of the invention are easily prepared; the grease may be made at a shear rate below which at least one other polyurea type grease is normally made.

What is claimed is:

1. A grease composition comprising a major portion of a lubricating oil base vehicle and a minor amount of the product obtained by reacting a compound (A) having the formula $NH_2R_1$, wherein $R_1$ is hydrocarbyl containing 3 to 30 carbon atoms, a compound (B) having the formula $NH_2-C_3H_6NR_3C_3H_6NH_2$ wherein $R_3$ is methyl, ethyl, or n-propyl, and a compound (C) having the formula $OCN-R_2-NCO$, wherein $R_2$ is hydrocarbylene having from 2 to 30 carbon atoms, the ratio of mols of (A): (B): (C) being about 2:1:2.

2. The composition of claim 1 wherein $R_1$ is aliphatic containing 10 to 30 carbon atoms, $R_2$ is alkylarylene containing 8 through 12 carbon atoms, and $R_3$ is methyl.

3. The composition of claim 2 wherein $R_1$ is stearyl and $R_2$ is tolylyl.

4. A grease composition comprising a major portion of a lubricating oil base vehicle and a minor amount of the product obtained by mixing a compound (A) having the formula $NH_2R_1$, wherein $R_1$ is hydrocarbyl containing 3 to 30 carbon atoms and a compound (B) having the formula $NH_2-C_3H_6NR_3C_3H_6NH_2$, wherein $R_3$ is methyl, ethyl, or n-propyl, and adding a compound (C) having the formula $OCN-R_2-NCO$, wherein $R_2$ is hydrocarbylene having from 2 to 30 carbon atoms, the ratio of mols of (A): (B): (C) being about 2:1:2.

5. The composition of claim 4 wherein $R_1$ is aliphatic containing 10 to 30 carbon atoms, $R_2$ is alkylarylene containing 8 through 12 carbon atoms, and $R_3$ is methyl.

6. A composition of claim 5 wherein $R_1$ is stearyl and $R_2$ is tolylyl.

7. A grease composition comprising a major portion of a lubricating oil base vehicle and a minor amount of the product obtained by reacting in the vehicle a compound (A) having the formula $NH_2R_1$, wherein $R_1$ is hydrocarbyl containing 3 to 30 carbon atoms, a compound (B) having the formula $NH_2-C_3H_6NR_3C_3H_6NH_2$ wherein $R_3$ is methyl, ethyl, or n-propyl, and a compound (C) having the formula $OCN-R_2-NCO$, wherein $R_2$ is hydrocarbylene having from 2 to 30 carbon atoms, the ratio of mols of (A): (B): (C) being about 2:1:2.

8. The composition of claim 7 wherein $R_1$ is aliphatic containing 10 to 30 carbon atoms, $R_2$ is alkylarylene containing 8 through 12 carbon atoms, and $R_3$ is methyl.

9. The composition of claim 8 wherein $R_1$ is stearyl and $R_2$ is tolylyl.

10. A grease composition comprising a major portion of a lubricating oil base vehicle and a minor amount of the product obtained by mixing in the vehicle a compound (A) having the formula $NH_2R_1$, wherein $R_1$ is hydrocarbyl containing 3 to 30 carbon atoms and a compound (B) having the formula $NH_2-C_3H_6NR_3C_3H_6NH_2$, wherein $R_3$ is methyl, ethyl, or n-propyl, and adding a compound (C) having the formula $OCN-R_2-NCO$, wherein $R_2$ is hydrocarbylene having from 2 to 30 carbon atoms, the ratio of mols of (A): (B): (C) being about 2:1:2.

11. The composition of claim 10 wherein $R_1$ is aliphatic containing 10 to 30 carbon atoms, $R_2$ is alkylarylene containing 8 through 12 carbon atoms, and $R_3$ is methyl.

12. The composition of claim 11 wherein $R_1$ is stearyl and $R_2$ is tolylyl.

* * * * *